United States Patent [19]

Haugwitz et al.

[11] 4,145,433
[45] Mar. 20, 1979

[54] METHOD OF TREATING HELMINTHIASIS BY PARENTERAL ADMINISTRATION OF SULFOXIDE DERIVATIVES OF BENZIMIDAZOLES

[75] Inventors: Rudiger D. Haugwitz, Titusville; Larry R. Cruthers, Flemington, both of N.J.

[73] Assignee: E. R. Squibb & Sons, Inc., Princeton, N.J.

[21] Appl. No.: 870,410

[22] Filed: Jan. 18, 1978

[51] Int. Cl.$^2$ .......................................... A61K 31/415
[52] U.S. Cl. ................................. 424/273 B; 548/306
[58] Field of Search .................. 424/273 R, 273 B; 548/306

[56] References Cited
U.S. PATENT DOCUMENTS

| 4,025,638 | 5/1977 | Gyurik et al. | 424/273 R |
| 4,046,908 | 9/1977 | Haugwitz et al. | 424/273 R |

*Primary Examiner*—Sam Rosen

*Attorney, Agent, or Firm*—Lawrence S. Levinson; Merle J. Smith; Burton Rodney

[57] ABSTRACT

A method is provided for treating or inhibiting helminthiasis by parenterally or topically administering sulfoxide derivatives of benzimidazoles having the structure

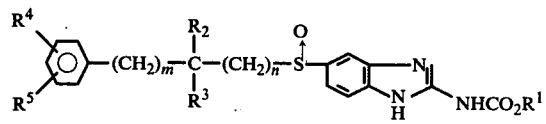

wherein $R^1$ is lower alkyl or phenyl-lower alkyl, $R^2$ and $R^3$ may be the same or different and are hydrogen or lower alkyl, $R^4$ and $R^5$ may be the same or different and are hydrogen, lower alkyl, lower alkoxy, halogen or nitro, and m is 0 to 3, n is 0 to 3, m + n being $\leq 5$. Pharmaceutical compositions for use in the above method are also provided.

12 Claims, No Drawings

METHOD OF TREATING HELMINTHIASIS BY PARENTERAL ADMINISTRATION OF SULFOXIDE DERIVATIVES OF BENZIMIDAZOLES

BACKGROUND OF THE INVENTION

Various benzimidazole compounds are known for their use an anthelmintic agent. For example, U.S. Pat. No. 3,574,845 to Actor et al and assigned to Smith Kline discloses 5(6)-benzene ring substituted benzimidazole-2-carbamate derivatives including 5(6)-methylthio-2-carboethoxyaminobenzimidazole and various 5(6)-alkyl-2-carbomethoxyaminobenzimidazoles.

U.S. Pat. Nos. 3,929,821 and 4,002,640 to Beard et al and assigned to Syntex disclose various 5(6)-benzene ring substituted benzimidazole-2-carbamate derivatives including 5(6)-alkylsulfinyl-2-carbomethoxyaminobenzimidazoles, as well as 5(6)-benzylsulfinyl-2-carbomethoxyaminobenzimidazole, 5(6)-phenylsulfinyl-2-carbomethoxyaminobenzimidazole, 5(6)-cycloalkylsulfinyl-2-carbomethoxyaminobenzimidazoles and 5(6)-cyclopropylmethyl-sulfinyl-2-carbomethoxyaminobenzimidazole.

The benzimidazoles mentioned above are said to be active orally.

Other benzimidazoles useful as anthelmintic agents are disclosed in U.S. Pat. Nos. 3,929,822, 3,929,823 3,929,824, 3,935,209, 3,965,113 and 4,005,202 all to Beard et al and assigned to Syntex; U.S. Pat. Nos. 3,682,952 to Actor et al, 3,578,676 and 3,694,455 to Dunn, 3,915,986 and 3,969,526 to Gyurik, all assigned to Smith Kline; and U.S. Pat. No. 3,738,993 to Haugwitz et al assigned to Squibb.

The aforementioned patents teach that the benzimidazole compounds disclosed therein are useful orally in treating helminthiasis.

U.S. Pat. Nos. 3,954,791 to Loewe et at and 3,928,375 to Duwel et al, both assigned to Hoechst disclose 2-carbalkoxy-amino-benzimidazole-5(6)-phenyl and phenylthio ethers which are said to be active perorally and subcutaneously.

In accordance with the present invention, it is indeed surprising that 5(6)-alkylsulfinyl-2-carbomethoxyaminobenzimidazoles may be effectively administered parenterally in the treatment or prevention of helminthiasis inasmuch as most benzimidazole compounds are active only upon oral administration.

DESCRIPTION OF THE INVENTION

The present invention relates to a method for treating or inhibiting helminthiasis by parenterally or topically administering to a mammalian host a sulfoxide derivative of a benzimidazole having the structure

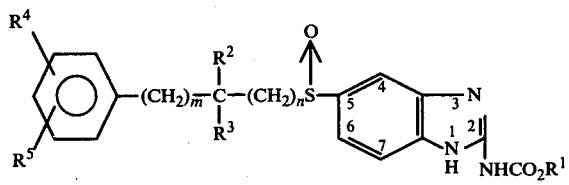

wherein $R^1$ is lower alkyl or phenyl-lower alkyl, $R^2$ and $R^3$ may be the same or different and are hydrogen or lower alkyl, and $R^4$ and $R^5$ may be the same or different and may be hydrogen, lower alkoxy, halogen or nitro, m is 0 to 3, n is 0 to 3 and m + n is $\leq$ 5.

The term "lower alkyl" as used herein includes straight or branched chain aliphatic hydrocarbon radicals having up to and including seven carbon atoms, such as methyl, ethyl, propyl, isopropyl, n-butyl, isobutyl, t-butyl, amyl, hexyl, heptyl and the like.

$(CH_2)_m$ and $(CH_2)_n$ represent a single bond or straight or branched chain alkylene radicals containing 3 or less carbons in the longest normal chain.

The term "lower alkoxy" as used herein includes any of the above lower alkyl groups linked to an oxygen atom.

The term "halogen" as used herein refers to Cl, Br, F and I, with Cl or Br being preferred.

Examples of compounds which may be employed in the method of the invention include the following.

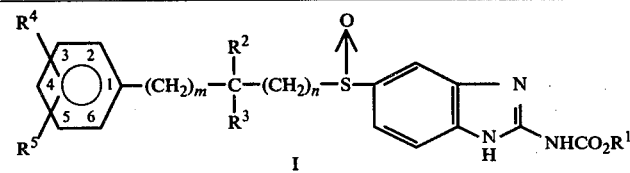

| | $R^1$ | $R^2$ | $R^3$ | $R^4$ (position) | $R^5$ (position) | $(CH_2)_m$ | $(CH_2)_n$ |
|---|---|---|---|---|---|---|---|
| 1. | $CH_3$ | H | H | H | H | — | — |
| 2. | $CH_3$ | H | H | H | H | — | — |
| 3. | $C_2H_5$ | $CH_3$ | H | $CH_3(4)$ | H | — | — |
| 4. | $C_3H_7$ | H | H | $CH_3(3)$ | $CH_3(5)$ | — | — |
| 5. | $CH_3$ | H | H | $NO_2(3)$ | H | — | — |
| 6. | $C_6H_5CH_2$ | H | H | $Cl(4)$ | H | — | — |
| 7. | $C_6H_5CH_2$ | H | H | $CH_3O(4)$ | H | — | — |
| 8. | $CH_3$ | H | H | H | $CH_3(4)$ | — | — |
| 9. | $CH_3$ | H | $C_2H_5$ | H | H | $CH_2$ | — |
| 10. | $C_2H_5$ | H | H | H | H | — | $CH_2$ |

The benzimidazole derivatives of structure I may be prepared as described in U.S. Pat. Nos. 3,929,821 and 4,002,640 to Beard et al.

In certain instances, the compounds of formula I form physiologically acceptable acid-addition salts with inorganic and organic acids. These salts frequently provide useful means for isolating the products from reaction mixtures by forming the salt in a medium in which it is insoluble. The free base may then be obtained by neutralization. Then any other salt may again be formed from the free base and the appropriate inorganic acid. Illustrative are the hydrohalides, especially the hydrochloride and hydrobromide which are preferred, sulfate, nitrate, tartrate, methanesulfonate, benzene-sulfonate, toluenesulfonate, and the like.

In accordance with the present invention, the compounds of formula I are administered parenterally, such as subcutaneously, intravenously, intramuscularly or interperitoneally, or topically (cutaneously), preferably directly on to exposed skin surface, to a mammalian host in the treatment and/or prevention of helminthiasis. Helminthiasis is a parasitic disease which causes widespread and often serious infection in domesticated animals, such as swine, horses, cattle, dogs, cats and sheep. The compounds administered parenterally or topically are useful in treating infections caused by Haemonchus, Ostertagia, Trichostrongylus, Cooperia, Dictyocaulus, Nematodirus, Bunostomum, Strongyloides, Oesophagostomum, Trichuris, and liver flukes.

In preparing injectable compositions, the compounds are mixed with a non-toxic, physiologically acceptable non-pyrogenic carrier such as sterile water, sterile saline solution, benzyl benzoate, 1,3-butylene glycol, ethyl oleate, castor oil, glyceryl triacetate, sesame oil, and sesame oil:benzyl benzoate (1:1). The parenteral product will usually take the form of a suspension containing from about 1 to about 10% by weight of the compound of formula I.

The above injectable compositions may also include a non-toxic physiologically acceptable non-pyrogenic suspending agent. Thus, where a non-oily carrier is employed such as water, suspending agents such as carboxymethyl cellulose, methyl cellulose, polyvinyl pyrrolidone or non-antigenic gelatin may be employed. Where the carrier employed is an oil, aluminum monostearate may be employed as a suspending agent. The suspending agent may be employed in amounts ranging from about 0.05 to about 2%, and preferably from about 0.1 to about 1% by volume of carrier (the above % may be based on the weight of the carrier where the carrier is qs to 100g).

A non-toxic, non-pyrogenic wetting agent may also be included in the injectable compositions in amounts ranging from about 0.005 to about 0.2% and preferably from about 0.01 to about 0.1% by weight of the carrier. Examples of suitable wetting agents include non-ionic surfactants such as polyoxyethylene sorbitan monostearate, polyoxyethylene sorbitan monooleate [e.g., Tweens] and fatty acid monoglycerides or diglycerides. Other surfactants suitable for use herein are disclosed in the published literature, for example, Kirk-Othmer, Encyclopedia of Chemical Technology, Second Edition, Volume 19, page 507 et seq.

In preparing topical or cutaneous compositions, the anthelmintic compounds are mixed with carriers which are effective in penetrating the skin, whereby the compounds are absorbed by the animal through the skin and transmitted systemically within the animal. A wide range of appropriate carriers may be employed to pass the compound through the skin. The composition employed may be a cream. A liquid composition, however, is particularly convenient to use, e.g., facilitating measuring out doses, and facilitating absorbance through the skin. Thus, a solution or suspension of the compound in a liquid carrier is preferred. Solutions are especially good for transmitting the compound through the skin and are therefore most preferred. The liquid carrier preferably comprises one or more liquids selected from hydrocarbons (e.g., armoatic hydrocarbons, such as an aromatic hydrocarbon fraction of boiling point 130°–250° C., e.g., 180°–220° C., xylene, benzene or toluene, or paraffins, such as those of 6–20 carbon atoms), halogenated aliphatic hydrocarbons (e.g., carbon tetrachloride), ketones (e.g., cyclohexanone or 2-butanone), esters (e.g., ethyl acetate, ethyl benzoate or triacetin), ethers (e.g., diisopropyl ether or tetrahydrofuran), alcohols (e.g., alkanols of 2–8 carbon atoms, such as butyl alcohol, amyl alcohol or isopropyl alcohol, or glycols, such as monopropylene glycol), amides (e.g., dimethylformamide), sulphones (e.g., dimethyl sulphone or sulpholane) and sulphoxides (e.g., dimethyl sulphoxide). In many cases a mixture of liquids is desirable. Preferably the liquid carrier comprises one or more liquids selected from hydrocarbons (e.g., aromatic hydrocarbons especially xylene), alcohols (e.g., isopropyl alcohol or amyl alcohol) and sulphoxides (e.g., dimethyl sulphoxide). Water tends to be ineffective as a liquid carrier for passing the compound through the skin of the animal. Accordingly, the carrier in the liquid compositions preferably comprises an organic liquid.

The viscosity of liquid compositions may be increased over what it would otherwise be by including thickeners which increase the viscosity. This may be desirable in order to retard or prevent the composition from running off the animal.

The additives may include, for example, a surface active agent, an animal fat or wax, e.g., lanolin, a mineral oil, e.g., liquid paraffin, a vegetable oil, e.g., peanut oil, olive oil, corn oil or castor oil, or a polymer, e.g., a hydrocarbon polymer such as polyisobutene.

The surface active agents may comprise anionic compounds for example, soaps, fatty sulphate esters, such as dodecyl sodium sulphate, fatty aromatic sulphonates such as alkylbenzene sulphonates or butyl-naphthalene sulphonates, more complex fatty sulphonates such as the amide condensation product of oleic acid and N-methyl taurine or the sodium sulphonate of dioctyl succinate.

The surface active agents may also comprise non-ionic surface active agents such as for example condensation products of fatty acids, fatty alcohols or fatty polyhydric alcohols, or the products obtained from the latter by condensation with ethylene oxide, or the products known as block copolymers of ethylene oxide and propylene oxide. The surface active agents may also comprise cationic agents such as, for example, cetyl trimethylammonium bromide.

The term "surface active agent" is used in the broad sense to cover materials variously called wetting agents, emulsifying agents and dispersing agents.

The composition may contain substances whose taste deters other animals from licking the composition off the animal treated. An example of such a substance is bitter aloes.

Generally, additives facilitating the use in pour-on formulations of other materials, e.g., systemic insecticides, active on animal physiology may be of use also in the present composition.

In general, in carrying out the method of the invention, the parenteral or topical composition described above will be administered to animals in a single dose to provide from about 1 to about 100 mg active compound per kilogram of animal body weight. It is preferred to employ in the range of 2.5-25 mg per kilogram of body weight. The compounds may be divided into a plurality of smaller doses given over one or more days, for example, up to 14 days.

The following examples are provided for illustrative purposes and may include particular features of the invention, however the examples should not be construed as limiting the invention, many variations of which are possible without departing from the spirit or scope thereof. All temperatures are in degrees centigrade.

EXAMPLE 1

Parenteral Composition Containing [5-[(Benzyl)sulfinyl]1H-benzimidazol-2-yl]carbamic acid, methyl ester A. [5-[(Benzyl)sulfinyl]-1H-benzimidazol-2-yl]carbamic acid, methyl ester (1) Preparation of benzyl methanesulfonate To an ice cooled solution of 54 g (0.5 mol) of benzyl alcohol and 75.75 g (104.3 ml, 0.75 mol) of triethylamine in 1800 ml of dichloromethane is added dropwise 63 g (42.57 ml, 0.55 mol) of methanesulfonyl chloride. The temperature of the reaction mixture during the addition is ca. 10°. The reaction mixture is then stirred for 1.5 hours at 10°. The reaction mixture is then diluted with dichloromethane, washed with ice water, cold 10% HCl, saturated $KHCO_3$, saturated NaCl and dried ($MgSO_4$). Solvent is removed in vacuo to yield the benzyl methanesulfonate as an oil.

(2) Preparation of 4-(Benzyl)sulfenyl-2-nitroaniline

To a solution of 19.5 g (0.1 mol) 4-thiocyano-2-nitroaniline in 130 ml dimethylformamide is added 3.78 g (0.1 mol) sodium borohydride, all at once. The mixture is stirred for one-half hour, then 15.2 g (0.1 mol) benzyl methanesulfonate in 70 ml dimethylformamide is added. The solution is stirred at 30° for 3 hours, cooled and partitioned between water and dichloromethane. The layers are separated and the aqueous phase reextracted with dichloromethane. The organic phases are combined, washed with aqueous $K_2CO_3$, water and saturated NaCl, dried, filtered and stripped to yield 4-(benzyl)sulfenyl-2-nitroaniline.

(3) Preparation of 4-(Benzyl)sulfinyl-2-nitroaniline

To an ice-cold solution of 10.4 g (40 mMol) 4-(benzyl)-sulfenyl-2-nitroaniline in 150 ml methanol is added 8.98 g (42 mMol) sodium meta-periodate in 150 ml water. The resulting suspension is stirred at 5° C. for 42 hours, then partitioned between water and dichloromethane. The layers are separated and the aqueous layer reextracted. The organic layers are combined and washed with saturated NaCl, dried, filtered and stripped to yield 4-(benzyl)sulfinyl-2-nitroaniline.

(4) Preparation of 4-(Benzyl)sulfinyl-1,2-diaminobenzene

To a solution of 7.18 g (26 mMol) 4-(benzyl)sulfinyl-2-nitroaniline in 100 ml ethanol is added 15.39 g (88 mMol) sodium hydrosulfite in 100 ml $H_2O$ and 20 ml concentrated aqueous $NH_3$. The resulting solution is heated to reflux for 1 hour, cooled, alcohol stripped and the aqueous mixture extracted with dichloromethane to yield 4-(benzyl)-sulfinyl-1,2-diaminobenzene.

(5) Preparation of [5-[(Benzyl)sulfinyl]-1H-benzimidazol-2-yl]carbamic acid, methyl ester To 3.34 g (14.5 mMol) of 4-(benzyl)sulfinyl-1,2-diaminobenzene in 35 ml methanol and 0.84 ml acetic acid is added 3.11 g (16 mMol) 1,3-bis(methoxycarbonyl)-S-methyl isothiourea, and the resulting solution heated to reflux for 3 hours. The solvent is removed in vacuo, the solid digested with water and filtered and washed with ether. The resulting solid is recrystallized from ethanol to yield the title compound.

B. Parenteral Formulation of [5-[(Benzyl)sulfinyl]-1H-benzimidazol-2-yl]carbamic acid, methyl ester A suspension suitable for subcutaneous administration is prepared by dispersing 150 mg of [5-[(benzyl)sulfinyl]-1H-benzimidazol-2-yl]carbamic acid, methyl ester in about 10 ml of water for injection, USP. The resulting suspension contains 1.5% by weight of the benzimidazole compound.

EXAMPLE 2

Testing of Parenteral Formulation of [5-[(Benzyl)sulfinyl]-1H-benzimidazol-2-yl]carbamic acid, methyl ester The following test is carried out to determine the effectiveness of treating sheep infected with gastrointestinal nematodes by subcutaneously administering a single dose of an aqueous suspension of [5-[(benzyl)sulfinyl]-1H-benzimidazol-2-yl]carbamic acid, methyl ester prepared in Example 1 so as to inject 10 mg of the above benzimidazole compound per kg of body weight of the test animal.

Egg per gram of feces (EPG) counts are conducted 2-4 days (avg. 3) prior to subcutaneously administering the above benzimidazole compound in order to determine the degree of parasitism of the test animal. Generally, animals are used which have at least 10,000 eggs per gram of feces although, on occasion, lambs with 8-9,000 egg per gram can be used. An average pretreatment EPG is calculated for the test animal and medication is given according to individual body weight (10 mg/kg).

EPG's are conducted daily during the week the animal is on test and the final three (3) EPG's are used to calculate an average post-treatment EPG. The percent reduction in the EPG count for a given compound is calculated by taking the average pretreatment EPG and dividing this figure into the average post-treatment EPG and subtracting the quotient from 100.

The [5-[(benzyl)sulfinyl]-1H-benzimidazol-2-yl]-carbamic acid, methyl ester in the form of an aqueous suspension is found to be extremely effective in reducing the fecal egg count (EPG) when administered subcutaneously at 10 mg/kg.

EXAMPLE 3

A. Dermal Formulation of [5-[(Benzyl)sulfinyl]-1H-benzimidazol-2-yl]carbamic acid, methyl ester A solution for cutaneous administration is prepared by dissolving 327 mg of [5-[(benzyl)sulfinyl]-1H-benzimidazol-2-yl]carbamic acid, methyl ester in a solution of about 4cc xylene and 1 cc dimethyl sulfoxide.

B. Testing of Dermal Formulation of [5-[(Benzyl)sulfinyl]-1H-benzimidazol-2-yl]carbamic acid, methyl ester In a manner similar to that described in Example 2, the composition of Example 3A is tested to determine the effectiveness of treating sheep infected with gastrointestinal nematodes by cutaneously administering (by syringe directly onto a shaven exposed skin surface) a single dose of the above solution of [5-[(benzyl)sulfinyl]-1H-benzimidazol-2-yl]carbamic acid, methyl ester so as to provide 10 mg of the above benzimidazole compound per kg of body weight of the test animal.

The Example 3A topical formulation is found to be extremely effective in reducing the fecal egg count (EPG), when administered cutaneously at 10 mg/kg.

What is claimed is:

1. A method of treating helminthiasis, which comprises parenterally administering to a mammalian host an effective amount of a compound of the structure

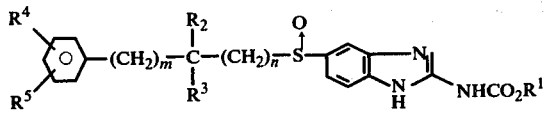

wherein $R^1$ is lower alkyl, phenyl-lower alkyl, $R^2$ and $R^3$ are the same or different and are selected from the group consisting of hydrogen and lower alkyl, and $R^4$ and $R^5$ may be the same or different and are selected from the group consisting of hydrogen, lower alkyl, lower alkoxy, halogen and nitro, m is 0 to 3, n is 0 to 3 and m + n is $\leq$ 5, dispersed in a non-toxic non-pyrogenic physiologically acceptable carrier.

2. The method as defined in claim 1 where in said compound $R^1$ is lower alkyl or benzyl.

3. The method as defined in claim 1 where in said compound $R^2$ and $R^3$ are hydrogen or methyl.

4. The method as defined in claim 1 where in said compound $R^4$ and $R^5$ are hydrogen.

5. The method as defined in claim 1 where in said compound m is 0 and n is 0, and $R^2$ and $R^3$ are hydrogen.

6. The method as defined in claim 1 wherein said compound has the name [5-[(benzylsulfinyl]-1H-benzimidazol-2-yl]carbamic acid, methyl ester.

7. The method as defined in claim 1 wherein said compound has the name [5-[(phenethyl)sulfinyl]-1H-benzimidazol-2-yl]carbamic acid, methyl ester.

8. The method as defined in claim 1 wherein said compound is administered subcutaneously.

9. The method as defined in claim 1 wherein said compound is administered intravenously.

10. An injectable composition for use in treating helminthiasis in mammalian species comprising an effective amount of a compound of the structure

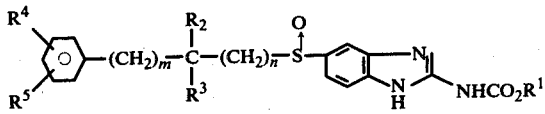

wherein $R^1$ is lower alkyl, phenyl-lower alkyl, $R^2$ and $R^3$ are the same or different and are selected from the group consisting of hydrogen and lower alkyl, and $R^4$ and $R^5$ may be the same or different and are selected from the group consisting of hydrogen, lower alkyl, lower alkoxy, halogen and nitro, m is 0 to 3, n is 0 to 3 and m + n is $\leq$ 5, and a non-toxic non-pyrogenic physiologically acceptable carrier therefor selected from the group consisting of benzyl benzoate, 1,3-butylene glycol, ethyl oleate, glyceryl triacetate, mixtures thereof, a mixture of benzyl benzoate and sesame oil, and sterile water for injection.

11. The composition as defined in claim 10 wherein said compound has the name [5-[(benzyl)sulfinyl]-1H-benzimidazol-2-yl]carbamic acid, methyl ester.

12. A method of treating helminthiasis, which comprises cutaneously administering to a mammalian host a compound of the structure

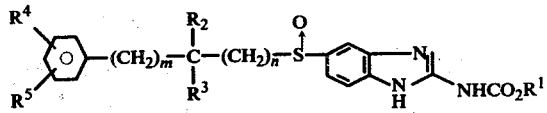

wherein $R^1$ is lower alkyl, phenyl-lower alkyl, $R^2$ and $R^3$ are the same or different and are selected from the group consisting of hydrogen and lower alkyl, and $R^4$ and $R^5$ may be the same or different and are selected from the group consisting of hydrogen, lower alkyl, lower alkoxy, halogen and nitro, m is 0 to 3, n is 0 to 3 and m + n $\leq$ 5, dispersed in a non-toxic non-pyrogenic physiologically acceptable carrier.

* * * * *